(12) United States Patent
Tretjak et al.

(10) Patent No.: US 10,508,074 B2
(45) Date of Patent: Dec. 17, 2019

(54) METHOD FOR PURIFYING (METH)ACRYLIC ESTERS

(71) Applicant: Arkema France, Colombes (FR)

(72) Inventors: Serge Tretjak, Roulhing (FR); Nathalie Hess, Chatrian (FR); Rose Aguiar, Meyzieu (FR); Pierre-Emmanuel Conoir, Metz (FR); Christophe Oses, Villeurbanne (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/068,974

(22) PCT Filed: Jan. 3, 2017

(86) PCT No.: PCT/FR2017/050005
§ 371 (c)(1),
(2) Date: Jul. 10, 2018

(87) PCT Pub. No.: WO2017/125657
PCT Pub. Date: Jul. 27, 2017

(65) Prior Publication Data
US 2019/0016665 A1 Jan. 17, 2019

(30) Foreign Application Priority Data
Jan. 20, 2016 (FR) .................... 16 50469

(51) Int. Cl.
*C07C 67/54* (2006.01)
*C07C 67/08* (2006.01)
*B01D 3/14* (2006.01)
*B01D 5/00* (2006.01)

(52) U.S. Cl.
CPC .............. *C07C 67/54* (2013.01); *B01D 3/141* (2013.01); *B01D 5/006* (2013.01); *C07C 67/08* (2013.01)

(58) Field of Classification Search
CPC ............................... C07C 67/54; B01D 3/141
USPC ........................................................ 560/208
See application file for complete search history.

(56) References Cited

U.S. PATENT DOCUMENTS

2013/0245309 A1 9/2013 Chalfant et al.
2013/0284586 A1 10/2013 Lee et al.

FOREIGN PATENT DOCUMENTS

| JP | 2005239564 A | * | 9/2005 | ............. B01D 3/141 |
| WO | WO 2012/071158 A1 | | 5/2012 | |
| WO | WO-2012071158 A1 | * | 5/2012 | ............. C07C 67/54 |

* cited by examiner

Primary Examiner — Deborah D Carr
(74) Attorney, Agent, or Firm — Lynn B. Morreale

(57) ABSTRACT

The subject of the invention is a process for recovering/purifying a $C_1$-$C_4$ (meth)acrylic ester from a crude reaction mixture comprising said ester, the process being carried out using a purification system comprising a divided wall column and a decanter, resulting in a simplification of the process and in a high productivity of the ester produced corresponding to the standards in terms of purity. The invention also relates to a process for producing $C_1$-$C_4$ (meth)acrylic ester comprising this recovery/purification process.

11 Claims, 1 Drawing Sheet

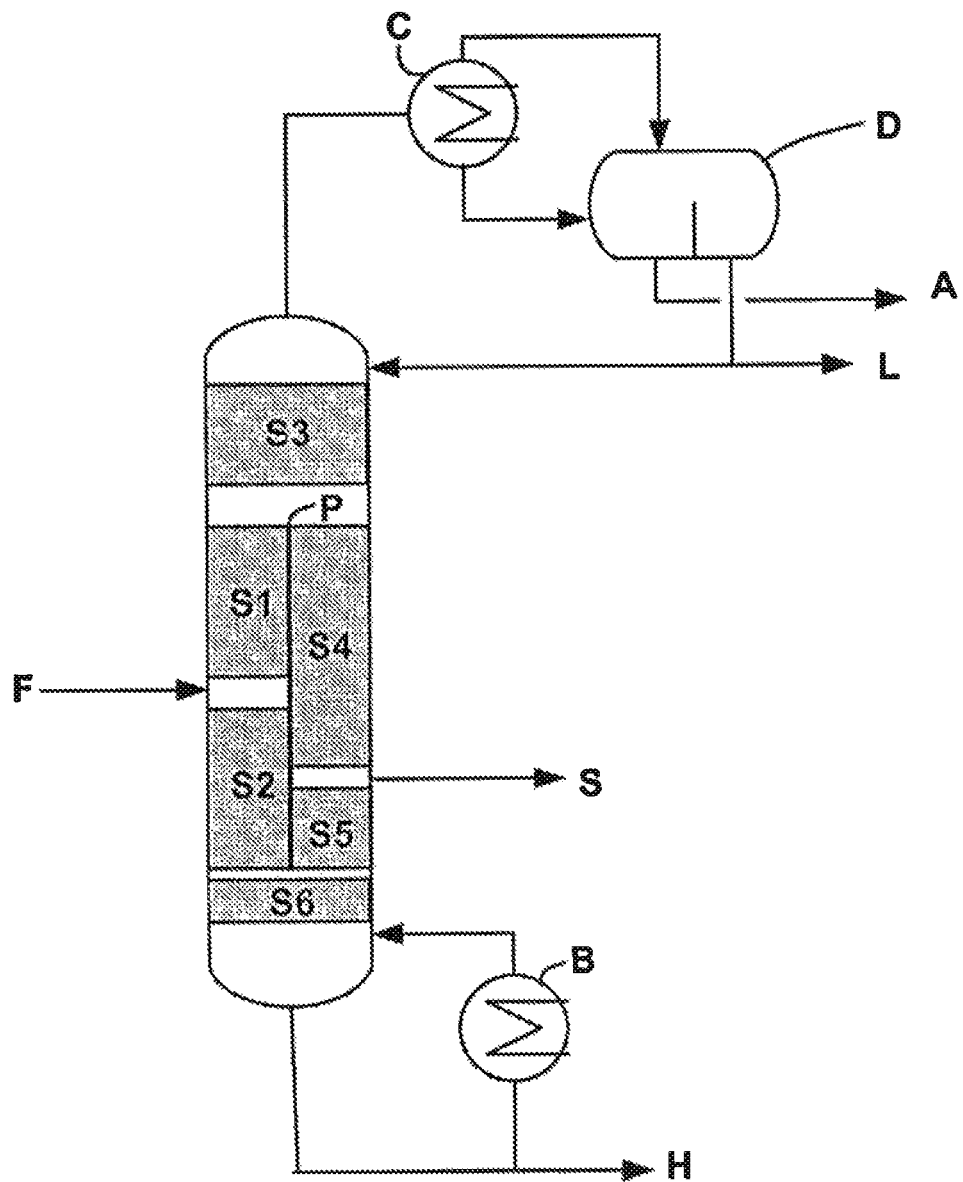

METHOD FOR PURIFYING (METH)ACRYLIC ESTERS

CROSS-REFERENCE TO RELATED APPLICATIONS

This application is a national stage application under 35 U.S.C. § 371 of PCT/FR2017/050005, filed Jan. 3, 2017 which claims benefit to application FRI 6.50469, filed Jan. 21, 2016.

TECHNICAL FIELD

The present invention relates to the production of $C_1$-$C_4$ (meth)acrylic esters by direct esterification of (meth)acrylic acid with the corresponding alcohol.

A subject of the invention is more particularly a process for recovering/purifying a $C_1$-$C_4$ (meth)acrylic ester from a crude reaction mixture comprising said ester, the process being carried out using a purification system comprising a divided wall column and a decanter, resulting in a simplification of the process and in a high productivity of the ester produced corresponding to the standards in terms of purity.

The invention also relates to a process for producing $C_1$-$C_4$ (meth)acrylic ester comprising this recovering/purifying process.

TECHNICAL BACKGROUND AND TECHNICAL PROBLEM

It is known practice to produce (meth)acrylic esters, in particular $C_1$-$C_4$ esters, generally known as light (meth)acrylic esters or light (meth)acrylates, such as methyl acrylate or methacrylate, and ethyl acrylate or methacrylate, by direct esterification of (meth)acrylic acid with the corresponding alcohol, catalysed for example by sulphuric acid or an ion exchange resin.

The esterification reaction generates water and is generally accompanied by side reactions which produce impurities, in particular heavy compounds, that is to say compounds which have a high boiling point, higher than that of the desired ester.

In such processes, a final product of high purity is sought, while at the same time optimizing the starting material balance.

For these purposes, the light compounds with a boiling point below that of the ester—mainly the unreacted reagents—are isolated so as to be recycled to the reaction, and the heavy products generated during the process are separated before being exploited by treatment for example on a film evaporator and/or thermal cracking.

Consequently, a combination of treatments of the crude reaction mixture resulting from the esterification reaction is generally carried out, by means of a combination of distillations and/or extractions, and separations by settling out, which is both relatively complex to implement, and costly in terms of energy.

Schematically, the purification of the crude reaction mixture generally comprises at least the following steps:

the crude reaction mixture is subjected to a distillation in a first column, termed topping column, making it possible to obtain:
  at the top, a stream composed essentially of light compounds;
  at the bottom, a stream comprising the desired ester, and heavy by-products;

the bottom stream from the topping column is subjected to a second column, termed rectification column, making it possible to separate:
  at the top, the desired purified ester;
  at the bottom, a stream containing essentially heavy by-products;

the light compounds of the top stream from the first column are at least partly recycled, after optional separation, to the reaction;

the bottom stream from the second column is subjected to various treatments with a view to exploiting the heavy by-products.

The use of these two columns in series has the drawback that the streams are subjected to high temperatures and to high residence times, in particular in the stripper associated with the first column, or at the bottom of the first column. The purified ester is obtained by distillation using the second column with elimination of heavy by-products. This heat exposure leads to the additional formation of heavy by-products by thermal 25 degradation, for example in the form of Michael adducts, thus reducing the purified-ester recovery yield and increasing the final amount of heavy impurities to be eliminated.

Moreover, the purification treatment needs to be controlled using stabilizers to limit the polymerization reactions that may occur under the operating conditions of the two columns. For this purpose, a first polymerization inhibitor, generally hydroquinone (HQ), is injected onto the first column, and a second polymerization inhibitor, generally methyl ether of hydroquinone (MEHQ), is injected onto the second column, resulting in a purified (meth)acrylic ester stabilized by methyl ether of hydroquinone which can be stored and transported before use.

A recent development in the distillation field has come to light under the name DWC (Divided Wall Column). This technology uses a single column, comprising an internal separating wall, which makes it possible to combine the operation of two columns that are conventionally in series, in a single piece of equipment, by using a stripper and a single condenser.

By way of example, patent application EP 2 659 943 describes a configuration of a divided wall column and the operation thereof in a process for producing 2-ethylhexyl acrylate of high purity. Although this column is complex to manufacture and to operate, it has the advantage of reducing the equipment cost and the energy consumption of the purification process, compared with a conventional facility comprising two distillation columns. The question of the stabilization required for it to function correctly is not, however, addressed. The purification process described in said document does not apply to the production of light acrylates by direct esterification. This is because, in the case for example of the synthesis of ethyl acrylate, the crude reaction medium comprises, in addition to the desired ethyl acrylate, also water produced by the reaction. Since ethyl acrylate and water have very close boiling points, separation of the water in a single column remains problematic.

Patent application JP 2005-239564 also describes the use of a divided wall column in a process for synthesizing (meth)acrylic esters, exemplified in the case of the synthesis of butyl methacrylate by transesterification reaction between methyl methacrylate and butanol. In this process, a demister is combined with the divided wall column so as to prevent the entrainment of stabilizer droplets in the sidestream withdrawal and to control the amount of stabilizers in the purified product. The divided wall column makes it possible to perform the separation of the targeted ester with the heavy products and the lighter products. The obtaining, by direct esterification of a light ester, such as ethyl acrylate with a boiling point close to that of water, corresponding to the commercial specifications is difficult to envisage in this process because of the presence of water that is difficult to eliminate using the divided wall column. It is recommended, in document JP 2005-239564, to eliminate the water beforehand using a solvent.

Document WO 2012/071158 describes a process for synthesizing $C_1$-$C_4$ alkyl (meth)acrylates, in particular butyl acrylate, in which the problem of the water arises during the esterification reaction step. Indeed, it is necessary to eliminate the water in order to shift the equilibrium of the reaction, but it is also necessary to keep the water in the reactor in order to promote certain azeotropes and to prevent the loss of ester and of alcohol at the top of the column. This is carried out by placing a decanter at the top of the reactor-distillation column assembly in order to separate an aqueous phase which is sent by reflux into the top of the column. The column surmounting the reactor may be a conventional column or a divided wall column, but it does not have the function of purifying the reaction mixture. In the process of document WO 2012/071158, the purified ester is obtained in a conventional purification section from the organic phase separated using the decanter placed at the top of the distillation column surmounting the reactor.

In the prior art documents, the additional problem of the separation of the water in a divided wall column for a process for producing light acrylates by direct esterification does not arise. Moreover, the presence of water in the medium to be treated requires more complex stabilization in order to limit polymerization reactions. It is necessary, on the one hand, to use a stabilizer for the organic medium and the aqueous medium that are present at the top of the column and, on the other hand, to stabilize the purified ester in order to obtain a "commercial" quality.

To the knowledge of the inventors, a purification technique combining a divided wall column and a decanter has never been used for purifying light (meth)acrylic esters, in particular ethyl acrylate, and the question of the stabilization required for it to operate correctly has not been addressed in the prior art.

The objective of the present invention is thus to provide a process for recovering a $C_1$-$C_4$ (meth)acrylic ester purified using a purification system comprising a divided wall column and a decanter.

The present invention thus provides a technico-economic solution to the problem of the purification of a crude reaction mixture resulting from the reaction of esterification of (meth)acrylic acid with a $C_1$-$C_4$ alcohol.

SUMMARY OF THE INVENTION

A subject of the invention is a process for recovering a purified $C_1$-$C_4$ (meth)acrylic ester from a crude reaction mixture obtained by direct esterification of (meth)acrylic acid with the corresponding alcohol, characterized in that it is carried out by means of a purification system comprising:
- a divided wall column equipped with an internal partial partition creating separation zones in the column, and combined, at the bottom, with a single boiler and, at the top, with a single condenser, said divided wall column comprising a common rectification section above the partition, a prefractionation section comprising the column feed, a withdrawal section separated from the prefractionation section by the partition, comprising the withdrawal of the purified ester, and a common stripping section below the partition; and
- a decanter placed at the outlet of the top condenser.

According to one embodiment, the stabilization of the purification system is carried out using a single polymerization inhibitor, preferably injected at the top condenser, the purified (meth)acrylic ester being withdrawn laterally from the divided wall column in the form of an already stabilized liquid or gas stream.

According to one embodiment, the stabilization of the purification system is carried out using a first polymerization inhibitor, preferably injected at the top condenser, the purified (meth)acrylic ester being withdrawn laterally from the divided wall column in the form of a gas stream which, after condensation, is then stabilized with a polymerization inhibitor different from the first inhibitor.

The process according to the invention applies to the synthesis of light alkyl (meth)acrylates, the esterifying alcohol being a primary or secondary aliphatic alcohol comprising a linear or branched alkyl chain comprising from 1 to 4 carbon atoms. As examples of alcohols, mention may be made of methanol, ethanol, propanol, isopropanol, n-butanol and secondary butanol.

The alcohol is preferably ethanol.

Acrylic acid is preferably used.

The recovery process according to the invention results in a $C_1$-$C_4$ (meth)acrylate which has a purity at least equivalent to that obtained in a conventional facility comprising two distillation columns, this being under operating conditions which minimize the heat degradation of the heat-sensitive compounds, and under more economical energy conditions.

Furthermore, the inventors have discovered that the stabilization of the purification system combining a divided wall column and a decanter is more advantageous than the stabilization of a conventional facility comprising two columns in series. Indeed, the polymerization inhibitor used to stabilize the desired ester can be introduced into the purification system as a single polymerization inhibitor, this results in simplification and consistency of the stabilization. As an alternative, a less expensive polymerization inhibitor can be used to stabilize the divided wall column, and the purified ester is then stabilized with another compound which is more suitable for stabilizing the final product with a view to its storage and subsequent use. In this case, the cost associated with the polymerization inhibitors can be greatly reduced.

Another subject of the invention is a process for producing a purified $C_1$-$C_4$ (meth)acrylic ester by direct esterification of (meth)acrylic acid with the corresponding alcohol, characterized in that the crude reaction mixture is subjected to the recovery process by means of the purification system as defined above.

Thus, the invention makes it possible to achieve the desired specifications in terms of purity of the light (meth) acrylic esters under economical conditions.

BRIEF DESCRIPTION OF THE FIGURES

FIG. 1 represents an example of a configuration of a purification system comprising a divided wall column and a decanter that can be used in the process according to the invention.

DETAILED DISCLOSURE OF THE INVENTION

The invention is now described in greater detail and in a non-limiting manner in the description which follows.

With reference to FIG. 1, the divided wall column comprises a partial vertical partition (or wall) P, placed inside the column, thus defining four distinct zones: an upper zone, a central zone comprising two zones on either side of the partition, and a lower zone. According to one embodiment, the partition may be partly diagonal. The partition may be flat or cylindrical such that the spaces separated by the partition may be arranged in concentric form.

The partition as installed does not necessarily separate the central zone into two equal zones, it may in fact be advantageous, in certain embodiments, to have unequal zones in order to minimize the pressure drop or the tendency to clog depending on the nature or the strength of the streams circulating in the column.

The central zone consists of two zones on either side of the partition, one of which represents a "prefractionation" section and the other of which represents a section for withdrawal of the pure product.

The prefractionation section comprises the feed F of the column, thus separating a section S1 above the feed and a section S2 below the feed. The prefractionation section has the effect of concentrating the most volatile products, termed light compounds, and also the water, at the top of the column, and of concentrating the least volatile products, termed heavy compounds, at the bottom of the column.

The withdrawal section comprises a lateral outlet in order to withdraw the purified ester S, the lateral outlet dividing the withdrawal section into two sections S4 and S5. The withdrawal of the purified ester can be carried out in the form of a liquid stream or of a gas stream, a gas stream is preferably withdrawn. In this section, the light compounds and also the water are sent to the top of the column and the heavy compounds are sent to the bottom of the column.

Above the partition at the top of the divided wall column is a common zone, termed rectification section S3, which makes it possible to separate the light compounds which are condensed in the condenser C combined with the column.

The decanter D, placed at the outlet of the condenser C, is used to separate, continuously or batchwise, an aqueous phase A and to ensure reflux of a part of the organic phase L comprising the light compounds at the level of the rectification section S3, the other part of the organic phase L being withdrawn. The aqueous phase A can be sent, continuously or batchwise, to a biological station. The liquid reflux on the prefractionation and withdrawal sections (not represented) is provided by a collecting means which makes it possible to distribute in a controlled manner the liquid from the bottom of the rectification section to the prefractionation and withdrawal sections. In the absence of the decanter D, it would not be possible to separate, at the top of the divided wall column, the water and the organic phase by a simple distillation operation because of the equivalent boiling points of the ester and of water.

The bottom of the divided wall column constitutes a common stripping section S6 which makes it possible to distribute the vapour derived from the boiler B placed at the bottom of the column in the prefractionation and withdrawal sections. A stream consisting essentially of the heavy compounds H is withdrawn at the bottom of the column.

A certain number of parameters characterize the design and the operation of the divided wall column. These are mainly the number of theoretical stages in each section of the divided wall column, in particular the numbers N1, N2, N3, N4, N5 and N6 corresponding respectively to the number of stages of each of the sections S1 to S6 previously described, the degree of reflux of the column, the ratio of liquid stream originating from the rectification section on each side of the partition, the ratio of gas stream originating from the stripping section on each side of the partition, or the position of the feed point F or of the point of lateral withdrawal S of the pure product.

These various parameters can be determined using methods known by those skilled in the art in such a way that the (meth)acrylic ester is produced with a purity that corresponds to the desired specifications.

The divided wall column and the internals present are chosen so as to obtain the number of theoretical stages required in each section. As internals, use may be made of plates, ordered packing such as structured packing or bulk packing.

According to one embodiment, the number of theoretical stages of the prefractionation section S1+S2 is between 1 and 10, and the feed of the column is preferably placed in approximately the first third of this section.

According to one embodiment, the number of theoretical stages of the withdrawal section S4+S5 is between 2 and 15, and the point of withdrawal of the purified ester is preferably placed at approximately ¾ of this section.

According to one embodiment, the number of theoretical stages of the rectification section S3 is between 5 and 15.

According to one embodiment, the number of theoretical stages of the stripping section S6 is between 2 and 10.

The column can operate under vacuum, in order to minimize the heat exposure of the heat-sensitive compounds within the column. Advantageously, the column operates under a vacuum ranging from 100 to 500 mmHg (or 130 mbar to 755 mbar).

Advantageously, the operating temperature is between 50° C. and 120° C.

The internals used for the column may be either valve plates or perforated plates with downcomer, or ordered packing, for instance structured packing such as Mellapack 250X from Sulzer.

The decanter placed at the outlet of the condenser may be a horizontal decanter with interface regulation which allows constant withdrawal of the aqueous phase and of the organic phase which is partially sent back into the column.

This decanter may also be, in the case of batchwise operation, a tank equipped with an overflow for redistributing the organic phase and with an emptying system at the bottom of the tank that will make it possible to intermittently remove the water.

In the interests of simplicity of the remainder of the disclosure, and in a non-limiting manner, the process of the invention is described with reference to a process for producing $C_1$-$C_4$ acrylic ester, and in particular to the production of ethyl acrylate from acrylic acid and ethanol.

By way of side reactions that result in the formation of heavy by-products during the production of ethyl acrylate, this involves essentially the formation of oligomers of unreacted acrylic acid, in the form of acrylic acid dimer (3-acryloxypropionic acid, n=1) and to a lesser extent of acrylic acid trimer (3-acryloxy-3-propoxypropionic acid, n=2), but also Michael addition reactions (Michael adducts), in particular between the ethyl acrylate already formed and the unreacted ethanol, resulting in ethyl ethoxypropionate, or the formation of 2-ethoxyethanol.

The light compounds present in the reaction medium are generally the residual reagents—acrylic acid and ethanol— the ethyl acrylate and the water generated by the reaction.

Besides the operating conditions suitable for the esterification reaction minimizing the formation of heavy compounds and optimizing the reaction yield, it is necessary to introduce polymerization inhibitors (also called stabilizers)

not only during the reaction, but also during the purification of the crude reaction mixture leaving the esterification reactor.

As polymerization inhibitors that can be used, mention may for example be made of phenothiazine, hydroquinone (HQ), monomethyl ether of hydroquinone (MEHQ), di-tert-butyl para-cresol (BHT), para-phenylenediamine, TEMPO (2,2,6,6-tetramethyl-1-piperidinyloxy), di-tert-butylcatechol, or TEMPO derivatives, such as OH-TEMPO, alone or mixtures thereof in any proportions.

Advantageously, from 500 to 5000 ppm of polymerization inhibitor are introduced during the purification of the reaction mixture in the purification system according to the process of the invention.

According to a first embodiment, a single stabilizer is used, injected at the top condenser, the purified ethyl acrylate being withdrawn laterally from the withdrawal section in the form of a liquid stream or of a gas stream. The purified ethyl acrylate is then directly stabilized and capable of being stored for subsequent use. According to this embodiment, monomethyl ether of hydroquinone is preferably used as stabilizer.

According to a second embodiment, a first polymerization inhibitor is used, injected at the top condenser, in order to limit the polymerization side reactions in the divided wall column, and the purified ethyl acrylate is withdrawn laterally in the form of a gas stream which, after condensation, is stabilized with a polymerization inhibitor different from the previous one injected into the top condenser. According to this embodiment, it is possible to use a much cheaper first inhibitor and to dispense with its presence in the purified product by performing a gas-phase withdrawal, the first polymerization inhibitor remaining in the stream of heavy by-products that is separated at the bottom of the column. Hydroquinone is suitable as first polymerization inhibitor since it also makes it possible to stabilize the aqueous phase originating from the presence of water at the top of the column. The ethyl acrylate withdrawn is then stabilized according to conventional practice, for example using methyl ether of hydroquinone.

The term "purified (meth)acrylic ester" is intended to mean a product having a (meth)acrylic ester content >99.9% by weight, and generally the following impurity contents: alkyl acetate<230 ppm, alkyl crotonate<170 ppm.

A subject of the invention is also a process for producing a purified $C_1$-$C_4$ (meth)acrylic ester, by direct esterification of (meth)acrylic acid with the corresponding alcohol, characterized in that the crude reaction mixture is subjected to the recovery process using a purification system as previously defined.

The esterification reaction conditions are those known by a person skilled in the art, and can be implemented according to a process of continuous, semi-continuous or batchwise type.

The invention thus provides a process for producing a $C_1$-$C_4$ (meth)acrylic ester in a compact facility, the investment and operating cost of which is reduced, and which provides a product of high purity with an optimized yield.

The examples hereinafter illustrate the present invention without, however, limiting the scope thereof.

Experimental Section

In the examples, the percentages are indicated by weight unless otherwise indicated and the following abbreviations have been used:
EA: ethyl acrylate
EOH: ethanol
EAC: ethyl acetate
EPRO: ethyl propionate
EPE: ethyl ethoxypropionate
ECROTONA: ethyl crotonate
Furfural: furfural
HQ: hydroquinone
MEHQ: methyl ether of hydroquinone Example 1 (Comparative)

A crude reaction mixture of ethyl acrylate from the synthesis by direct esterification of acrylic acid with ethanol was subjected to a purification treatment using two distillation columns in series.

The first column comprises a theoretical-stage equivalent of 15 and it is combined at the bottom with a boiler, and at the top with a condenser/decanter in which an organic phase is separated and recycled, in part, in the column in order to ensure reflux thereof. The column is stabilized by injection of HQ at the top condenser. The energy supplied by the boiler is 2.94 Gcal/h.

The second column comprises a theoretical-stage equivalent of 10 and it is combined at the bottom with a boiler and at the top with a condenser. It is fed by the stream from the bottom of the first column which comprises the EA, and also the heavy by-products such as furfural, EPE and the HQ stabilizer. The second column is stabilized by injection of MEHQ at the top condenser. The energy supplied by the boiler is 1.67 Gcal/h.

The feed of the first column has the following weight composition and characteristics:
EA: 93.88%-EOH: 0.26%-EAC: 0.38%-EPRO: 0.4%-EPE: 2.02%-Furfural: 0.05%-ECROTONA: 0.34%-water: 3.02%
Total flow: 12 983 kg/h-temperature: 72.2° C.-pressure: 0.394 bar.

An ASPEN simulation using the NRTL thermodynamic model was carried out and gives the following weight composition for the purified product distilled at the top of the second column.
EA: 99.91%-EOH: nothing-EAC: 0.0232%-EPRO: 0.04%-EPE: 0.002%-Furfural: nothing-ECROTONA: 0.0168%-MEHQ: 0.002%
Total flow: 12 069 kg/h
Temperature: 35° C.
Pressure: 0.394 bar.

In this configuration, the EA is recovered with a yield of about 98.9% relative to the feed stream, and the EA has a purity greater than 99.9%.

Example 2 (According to the Invention)

An ASPEN simulation using the NRTL thermodynamic model was carried out on the same crude reaction mixture of ethyl acrylate as that described in Example 1, but subjected to a purification using the purification system as represented in FIG. 1.

In this example, the divided wall column is stabilized at the level of the top condenser with HQ, and the ethyl acrylate withdrawn laterally in the gas phase is stabilized with MEHQ.

In this configuration, the number of plates of the various sections is as follows:
N1: 2-N2: 5-N3: 9-N4: 6-N5: 2-N6: 6
The energy supplied by the boiler is 3.3 Gcal/h.

The laterally withdrawn purified product has the following weight composition:

EA: 99.92%-EOH: nothing-EAC: 0.0223%-EPRO: 0.04%-EPE: 0.001%-Furfural: nothing-ECROTONA: 0.0149%-MEHQ: 0.002%

Total flow: 12 065.8 kg/h
Temperature: 76.8° C.
Pressure: 0.393 bar.

In this configuration, the EA is recovered with a yield of about 98.9% relative to the feed stream, and the EA has a purity greater than 99.9/o.

Compared with the conventional process, the heat required for the boiler in order to perform the purification is reduced by about 28% (3.3 Gcal/h compared with 4.61 Gcal/h), which brings about a more economical operational energy cost.

The invention claimed is:

1. A process for recovering a purified $C_1$-$C_4$ (meth)acrylic ester from a crude reaction mixture obtained by direct esterification of (meth)acrylic acid with the corresponding alcohol, carried out by a purification system comprising:
a divided wall column equipped with an internal partial partition creating separation zones in the column, and combined, at the bottom, with a single boiler and, at the top, with a single condenser, said divided wall column comprising a common rectification section above the partition, a prefractionation section comprising the column feed, a withdrawal section separated from the prefractionation section by the partition, comprising the lateral withdrawal of the purified ester from the divided wall column, and a common stripping section below the partition; and
a decanter placed at the outlet of the top condenser to separate, continuously or batchwise, an aqueous phase and to reflux part of an organic phase comprising light compounds at a level of the rectification section, other parts of the organic phase being withdrawn.

2. A process according to claim 1, having a number of theoretical stages of the rectification section of between 5 and 15.

3. A process according to claim 1 having a number of theoretical stages of the prefractionation section of between 1 and 10.

4. A process according to claim 1 having a number of theoretical stages of the withdrawal section of between 2 and 15.

5. A process according to claim 1 having a number of theoretical stages of the stripping section of between 2 and 10.

6. A process according to claim 1 wherein stabilization of the purification system is carried out using a single polymerization inhibitor, injected at the top condenser, the purified (meth)acrylic ester being withdrawn laterally from the divided wall column in the form of an already stabilized liquid or gas stream.

7. A process according to claim 6, wherein methyl ether of hydroquinone is used as polymerization inhibitor.

8. A process according to claim 1 wherein stabilization of the purification system is carried out using a first polymerization inhibitor, injected at the top condenser, the purified (meth)acrylic ester being withdrawn laterally from the divided wall column in the form of a gas stream which, after condensation, is then stabilized with a polymerization inhibitor different from the first inhibitor.

9. A process according to claim 8, wherein the first inhibitor is hydroquinone, and the purified (meth)acrylic ester is stabilized with methyl ether of hydroquinone.

10. A process according to claim 1 wherein the $C_1$-$C_4$ (meth)acrylic ester is ethyl acrylate.

11. A process for producing a purified $C_1$-$C_4$ (meth)acrylic ester by direct esterification of (meth)acrylic acid with the corresponding alcohol, wherein the crude reaction mixture is subjected to the recovery process using the purification system according to claim 1.

* * * * *